United States Patent [19]

Melcher

[11] Patent Number: 4,819,478
[45] Date of Patent: Apr. 11, 1989

[54] MEMBRANE ASSISTED FLOW INJECTION ANALYSIS

[75] Inventor: Richard G. Melcher, Midland, Mich.

[73] Assignee: The Dow Chemical Company, Midland, Mich.

[21] Appl. No.: 164,151

[22] Filed: Mar. 4, 1988

[51] Int. Cl.[4] .......................................... B01D 15/08
[52] U.S. Cl. ................................ 73/61.1 C; 210/635; 210/198.2
[58] Field of Search .................... 73/61.1 C; 210/635, 210/198.2, 198.3, 656, 659; 422/70; 436/161; 55/386

[56] References Cited

U.S. PATENT DOCUMENTS

| | | | |
|---|---|---|---|
| 4,070,284 | 1/1978 | Fujita et al. | 210/659 |
| 4,257,257 | 3/1981 | Dairaku et al. | 73/19 |
| 4,451,374 | 5/1984 | Peterson et al. | 210/198.2 |
| 4,529,521 | 7/1985 | Cortes et al. | 210/635 |
| 4,533,518 | 8/1985 | Hanaoka et al. | 210/198.2 |
| 4,715,217 | 12/1987 | Coyne et al. | 73/61.1 C |
| 4,775,476 | 10/1988 | Melcher et al. | 210/635 |

OTHER PUBLICATIONS

Leonard T. Skeggs, Jr., Ph.D., "An Automatic Method for Colorimetric Analysis", Am. J. Clin. Pathol, vol. 28, 1957, pp. 311–322.

W. E. Van Der Linden, "Membrane Separation in Flow Injection Analysis", Analytica Chimica Acta, vol. 151, 1983, pp. 359–369.

*Primary Examiner*—Stewart J. Levy
*Assistant Examiner*—Hezron E. Williams
*Attorney, Agent, or Firm*—Timothy S. Stevens

[57] ABSTRACT

A method for rapid and sensitive membrane assisted Flow Injection Analysis. A sample, containing a component to be analyzed, is injected into a flowing stream of carrier liquid and flowed past one side of a two-sided membrane. A receiving liquid is flowed past the other side of the membrane. The component to be analyzed is absorbed by the membrane from the carrier stream, is desorbed into the receiving stream and is carried to a detector for analysis in less than about 5 minutes. Critically, the partition coefficient of the component to be analyzed between the membrane and the receiving liquid is less than about $1 \times 10^1$.

10 Claims, 3 Drawing Sheets

MEMBRANE ASSISTED FLOW INJECTION ANALYSIS

FIELD OF THE INVENTION

The invention is in the field of continuous flow analysis and more specifically in the field of membrane assisted continuous flow analysis.

BACKGROUND OF THE INVENTION

Membrane assisted continuous flow analysis was probably first described by Skeggs in 1957 in his famous paper on Segmented Continuous Flow Analysis (SCFA), *Am. J. Clin. Pathol.*, 28, pp. 311–322. A pumped stream of liquid sample, sample conditioning liquid and air were joined to form an air segmented mixed stream that was then exposed to one side of a two-sided membrane. The other side of the membrane was exposed to an air segmented receiving stream of liquid which was subsequently directed to a flow-through detector. A component of interest in the sample permeated through the membrane under essentially steady state conditions into the liquid segments of the receiving stream to form a permeated sample component stream. Then a color forming reagent was added to the permeated sample component stream to form a colored reaction product stream which was flowed to the detector so that the concentration of the reaction product could be determined. The membrane serves an important function in membrane assisted continuous flow analysis. The membrane essentially blocks permeation of components of the sample that would otherwise interfere with the analysis, e.g., particulates in the sample. At the same time, the membrane allows permeation of a component of interest in the sample or a reaction product of the component of interest.

More recently, Flow Injection Analysis (FIA), also a continuous flow procedure but without air segmentation, has proved to be a formidable contender to SCFA (see U.S. Pat. No. 4,022,575 to Hansen and Ruzicka). In FIA, a liquid sample is injected into a flowing stream of liquid carrier. The liquid carrier usually contains a reagent so that the reagent can react with a component of the sample to form a reaction product. The flowing stream of liquid carrier is directed to a flow-through detector so that the reaction product can be determined. One advantage of FIA is that the injected sample disperses in a controlled manner with the carrier stream. Another advantage attributed to FIA is that any reaction need not be at steady state or be complete.

Membrane assisted Flow Injection Analysis is known using gas diffusion membranes, e.g., Van Der Linden, 1983, *Analytica Chimica Acta*, 151, pp. 359–369. In Van Der Linden's system, the sample, containing ammonia as the sample component of interest to be determined, is injected into a 0.1 Molar sodium hydroxide carrier stream and then flowed past a porous PTFE or a porous polypropylene gas diffusion membrane. The other side of the membrane is swept with a stream of 0.1 Molar sodium hydroxide receiving liquid to which stream is added a stream of Nessler's reagent prior to its flowing through a photometric detector set at 410 nanometers. Ammonia in the sample diffuses as a gas through the porous membrane to the receiving liquid and the Nessler's reagent forms a colored product when reacted with ammonia. Membrane assisted Flow Injection Analysis using a membrane where the component of interest in the sample is absorbed by the membrane has not been shown but has been suggested as will now be discussed.

Coyne et al., in U.S. Pat. No. 4,715,217, teach primarily a membrane assisted analytical chemistry method for the determination of the concentration of an organic compound in an aqueous matrix wherein the concentration of the organic compound is greater than the solubility limit of the organic compound. For this application the method of Coyne et al. is excellent. Coyne et al. taught injecting such a sample into a carrier stream containing an emulsifying agent so that the injected sample was carried past one side of a two-sided silicone rubber membrane (see Example 5). The other side of the membrane was swept with a gas receiving stream. An emulsified volatile component of the injected sample was absorbed by the membrane and then desorbed over an eight-minute time span into the gas receiving stream. The desorbed volatile component was carried to a cooled region where it was condensed and collected prior to analysis by gas chromatography. Coyne et al. stated (e.g., see column 3, lines 57–60) that the receiving stream on the other side of the membrane can be a gas for volatile sample components or a liquid for soluble sample components, and suggested (e.g., see column 4, lines 57–63) that the receiving stream could be sent directly to a detector to determine the volatile or soluble sample component that permeated through the membrane. Coyne et al. suggested that if the sample component of interest was below its solubility limit, an emulsifying agent is not necessary in the carrier (e.g., see column 1, lines 46–63). Thus, Coyne et al. also suggested a membrane assisted FIA method for determining the concentration of a sample component of interest below its solubility limit, comprising the steps of: injecting the sample into a flowing stream of liquid carrier; flowing the injected sample past one side of a two-sided membrane which absorbs a component of interest from the sample; flowing a liquid receiving stream past the other side of the membrane to a detector, so that the component of interest can be desorbed into the receiving stream and then be flowed to the detector for determination of the concentration of the permeated sample component.

Problems with this suggested membrane assisted FIA method are poor detection limits and increased analytical time due to the time needed to desorb the component of interest from the membrane with the liquid receiving stream. Coyne et al. refer to analytical times of from 8 to 20 minutes (using a gas receiving stream) but it would be preferable to have an analytical time much shorter than this and preferably less than 5 minutes.

SUMMARY OF THE INVENTION

The present invention is a membrane assisted FIA method that solves the above-mentioned problems of poor detection limits and increased analytical time with membrane assisted Flow Injection Analysis using an absorption type membrane. The method comprises four steps. The first step is to inject a predetermined volume of a liquid sample into a flowing stream of liquid carrier, e.g., a stream of water as the carrier, to form a dispersion of the sample in the carrier, the sample containing a component of interest, e.g., a sample of water containing trace levels of styrene monomer as the component of interest. The second step is to flow the dispersion of the sample in the carrier into fleeting contact with one side of a two-sided membrane, the membrane absorbing at least a portion of the component of interest from the dispersion of the sample in the carrier to form a dispersion of the component of interest in the membrane, e.g., styrene monomer in a silicone rubber membrane. The third step is to contact the other side of the membrane with a flowing stream of a receiving liquid, so that the dispersion of the component of interest in the membrane is essentially completely desorbed from the membrane in less than about five minutes and forming a dispersion of the component of interest in the receiving liquid, the partition coefficient of the component of interest between the membrane and the receiving liquid being less than about $1 \times 10^1$, e.g., using 50:50 acetonitrile:water as the receiving liquid with a silicone rubber membrane and styrene monomer as the component of interest. The fourth step is detecting the component of interest in the dispersion of the component of interest in the receiving liquid, e.g., flowing the receiving liquid through a UV liquid chromatography detector set to detect at 254 nm to determine the concentration of styrene monomer as the component of interest.

DETAILED DESCRIPTION OF THE INVENTION

Figure 1:
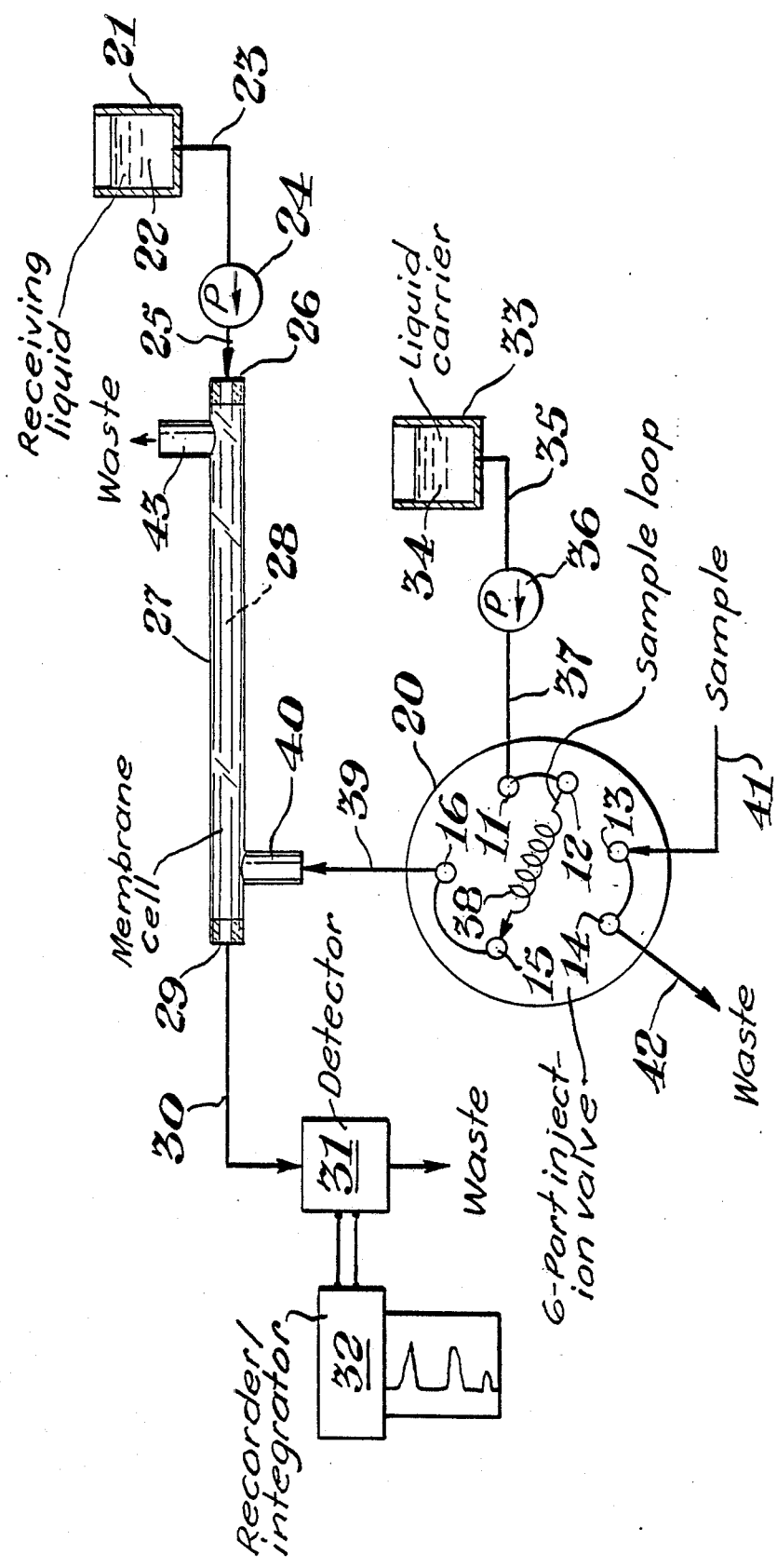
FIG. 1 is a schematic drawing of a preferred apparatus for carrying out the method of the present invention including a membrane cell and an integrator/recorder.

Referring now to FIG. 1, therein is shown a schematic drawing of a preferred apparatus used to carry out the method of the present invention, including a two-position, six-port valve 20 (such a valve is available from Anspec Co., Ann Arbor, MI, as the Cheminert Rotary Injection Valve, Catalog No. H1968) shown in the inject position. A receiving liquid reservoir 21 is provided for containing a receiving liquid 22. A length of tubing 23 connects the reservoir 21 with a receiving liquid pump 24 (available from Anspec, supra, as the Eldex Mode A pump, as Catalog No. F1111). The specific pumping means used here to flow the stream of receiving liquid is not critical in the invention and preferably is suitable for pumping the receiving liquid at a reasonably steady flow rate, e.g., most any liquid chromatography pump, a peristaltic pump and a gas pressurized reservoir 21. A restrictor may be required at the pump 24 outlet to induce a back pressure to allow the pump check valves to function properly. The pump 24 is connected (1/16 PTFE tubing and fittings used generally throughout herein for such connections and are available from Anspec, supra) to an inlet end 26 of a membrane cell 27 (shown in detail in FIG. 2) by a length of tubing 25. A tubular membrane 28 is connected to the inlet end 26 and an outlet end 29 of the cell 27. The outlet end 29 of the cell 27 is connected to a detector 31 by a length of tubing 30. The detector 31 communicates with a recorder/integrator 32 for data handling. A liquid reservoir 33 is provided for containing a liquid carrier 34. A length of tubing 35 connects the reservoir 33 with a liquid carrier pump 36 (available from Anspec, supra, as the FMI Jr. Lab Pump, Catalog No. F1106). The specific pumping means used here to flow the stream of liquid carrier is not critical in the invention and preferably is suitable for pumping the carrier at a reasonably steady flow rate, e.g., most any liquid chromatography pump, a peristaltic pump and a gas pressurized reservoir 33. The pump 36 is connected to port 11 of the valve 20 with a length of tubing 37. The valve 20 internally connects the valve ports as shown in FIG. 1, i.e., ports 11-12, 13-14, 15-16, and internally connects the ports 11-16, 12-13, 14-15 in the sample load position not shown. A sample loop 38 is connected to ports 12 and 15 of the valve 20. The sample loop 38 is a preferred means for injecting a preselected volume into a flowing stream of liquid, and this conduit can take other forms such as a conduit that is internally machined into a valve. The volume of sample injected can be as much as 1 milliliter or more but usually is less. A length of tubing 39 is used to connect port 16 of the valve 20 to the inlet arm 40 of the membrane cell 27. A length of tubing 41 is connected to port 13 of valve 20 for introducing a sample containing a sample component of interest into the sample loop 38 when the valve 20 is in the load position. The valve 20 is the preferred means for injecting a sample into the carrier stream. The specific means used for injecting a sample into the carrier is not critical and many different multiport valve constructions or other means can be used.

In FIG. 1, a flowing stream of the receiving liquid 22 from the pump 24 is shown being flowed through the bore of the tubular membrane 28, and then through the detector 31 to waste. In addition, liquid carrier 34 from pump 36 is flowed through the sample loop 38 and into the membrane cell 27, past the outside of the tubular membrane 28 and then out an outlet arm 43 to waste. When the valve 20 is switched into the sample load position, not shown, port 13 is connected to port 12 and port 15 is connected to port 14. This allows sample to flow through the sample loop 38 to waste through line 42. When the valve 20 is switched back to the inject position, shown in FIG. 1, a predetermined volume of the sample is injected into the flowing stream of liquid carrier 34 to form a dispersion of the sample in the carrier which is then flowed into fleeting contact with one side (the outside) of the tubular membrane 28 so that the membrane 28 absorbs at least a portion of the component of interest from the dispersion of the sample in the carrier to form a dispersion of the component of interest in the membrane 28. The term "fleeting contact" here and in the claims means that 90 percent of the dispersion of the sample in the carrier is in flowing contact with the membrane for less than five minutes and then rinsed past the membrane by the flow of more liquid carrier. As a practical matter, this contact time is usually substantially less than five minutes and can be reduced by increasing the pumping rate of the pump 36. The flowing stream of receiving liquid 22 on the other side of the tubular membrane 28 (the inside) desorbs the component of interest from the dispersion of the component of interest in the membrane to form a dispersion of the component of interest in the receiving liquid. Critically, this desorption must be substantially complete in less than about 5 minutes. Critically, the partition coefficient of the component of interest between the membrane and the receiving liquid must be less than about $1 \times 10^1$. The dispersion of the component of interest in the receiving liquid is then flowed to the detector 31 for determining the concentration profile of the dispersion of the component of interest in the receiving liquid. The detector 31 can be a liquid chromatography detector or a like flow-through device as is well understood by the art. Here and in the claims the term "substantially completely desorbed from the membrane is less than about 5 minutes" means that the triangulated concentration profile of the dispersion of the component of interest in the receiving liquid returns to baseline in less than about 5 minutes, as further discussed in Example 1. Here and in the claims, the term "the partition coefficient of the component of interest between the membrane and the receiving liquid" means: the concentration of the component of interest in the membrane divided by the weight of membrane, which product is then divided by the product of the concentration of the component of interest in the receiving liquid divided by the weight of the receiving liquid; for a test wherein 1.0 gram of shredded membrane, 10 grams of receiving liquid and a known representative weight of the component of interest are joined in a closed bottle and shaken for one hour before the concentration of the component of interest is then determined in the receiving liquid (and by inference also in the shredded membrane).

The specific liquid carrier used in the present invention is not critical as long as the component of interest is absorbed from the liquid carrier into the membrane. Water is a preferred liquid carrier and its pH can be modified to enhance absorption of the component of interest by the membrane, e.g., see Example 2. Salt can be added to the liquid carrier to enhance absorption of the component of interest by the membrane. The specific receiving liquid used in the present invention is not critical as long as the partition coefficient of the component of interest between the membrane and the receiving liquid is less than about $1 \times 10^1$. A preferred receiving liquid is water containing a polar solvent such as methanol, isopropanol or acetonitrile. The pH of the receiving liquid can be modified to reduce the partition coefficient, e.g., see Example 4. The receiving liquid can be a non-polar solvent such as hexane.

The specific membrane used is not critical in the invention as long as it allows rapid permeation of the component of interest in conjunction with the specific liquid carrier and receiving liquid used and as long as it is a homogeneous absorption type membrane such as a homogeneous rubber membrane and not a non-homogeneous (macroporous) membrane such as a macroporous PTFE or macroporous polyolefin gas diffusion membrane. An absorption type membrane absorbs the component of interest into the inner structure of the homogeneous membrane from the dispersion of the injected sample in the liquid carrier. A homogeneous absorption type membrane can be supported by a macroporous membrane or structure in the present invention, e.g., a macroporous tubular membrane can be coated with a homogeneous continuous film of silicone rubber or the pores of a macroporous tubular membrane can be impregnated with plugs of homogeneous silicone rubber or filled with a liquid such as silicone oil. The membrane can be planar in shape and can form a portion of a channel cut, for example, in a stainless steel or PTFE block. The membrane can be tubular in shape, and the tube can be relatively small in diameter, e.g., 0.05 inch or smaller. To produce sharp flow injection peaks, the preferred wall thickness of the membrane is 0.025 inch or less. The membrane can be hydrophilic or hydrophobic. A highly preferred membrane is a tubular silicone rubber membrane. The specific design of the membrane cell used is not critical in the invention. It can be made of materials such as glass, stainless steel or PTFE. The cell preferably is designed so that the dispersion of the injected sample in the liquid carrier intimately contacts the membrane. This can be achieved by making the carrier channel diameter only slightly larger than the diameter of a tubular membrane within the channel or by packing the channel, for example, with glass beads.

Figure 2:
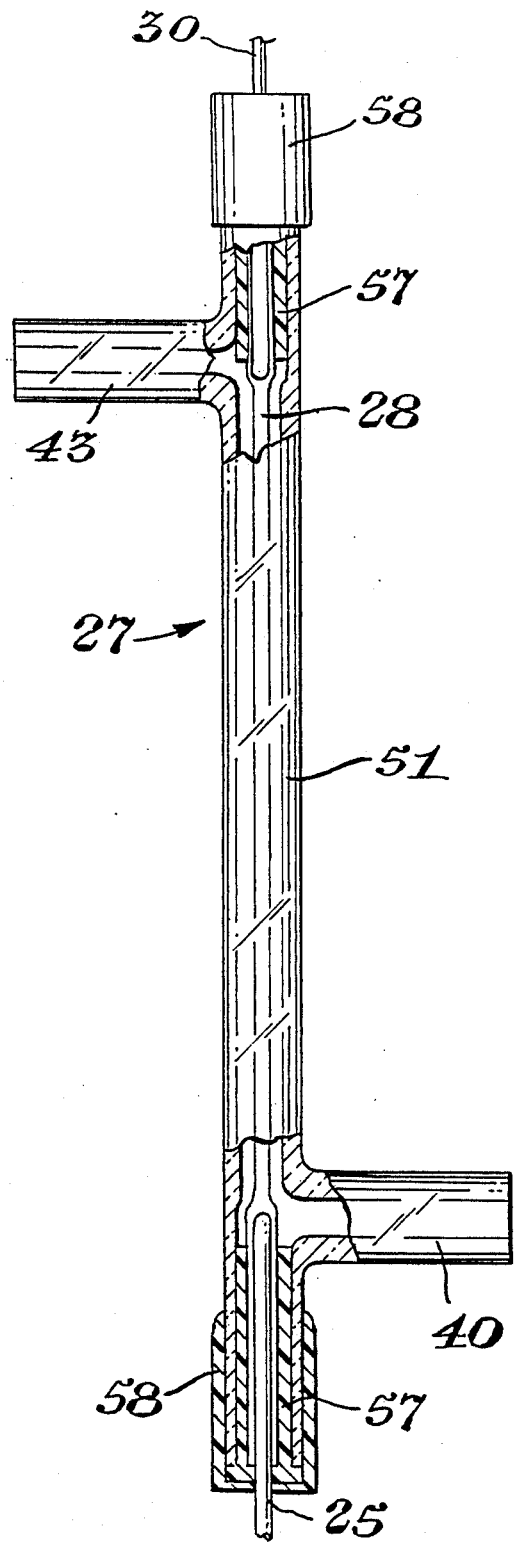
FIG. 2 is a side view, mostly in full and partly in section, of the membrane cell shown schematically in FIG. 1.

A preferred membrane cell 27 is shown in FIG. 2. A 180 mm long, 1 mm internal diameter glass tube 51 is provided with an inlet neck 40 and an outlet neck 43. A tubular membrane 28 is mounted in the cell 27 as shown and consists of Dow Corning Silastic ® Medical Tubing (0.012 inch internal diameter, 0.025 inch external diameter and about 180 mm long). Each end of the membrane 28 is connected to 1/32 inch outside diameter PTFE tubing 25 and 30 by first placing 3 cm of the membrane ends into xylene for approximately 3 minutes. The membrane, which is swollen with xylene, is slipped over the PTFE tubing for approximately 3 cm. When the xylene evaporates, a leak-tight joint is formed. The membrane 28, with the tubing 25 and 30 attached, is then inserted into the glass tube 51 and the ends of the tube 51 are each sealed with Dow Corning RTV ® Silicone Rubber Sealant 57. A plastic cap 58 is positioned at each end of the tube 51 to contain excess sealant 57. The other end of the tubing 25 and 30 is pulled into 1/16 inch diameter PTFE tubing (not shown) so that further connections can be made with 1/16 inch diameter tubing. The best membrane cells incorporating silicone rubber tubular membrane are made by stretching the membrane 28 so that it is about twice its unstretched length and holding the membrane in the stretched condition until the sealant 57 cures. A stretched silicone rubber membrane, of approximately the same final dimensions as an unstretched membrane in the cell 27, results in better sensitivity and faster return to baseline (see Example 5). This surprising result may be due to orientation of the polymer caused by the stretching but this is not known to be true. Stretching the membrane 28 also prevents the membrane 28 from deforming and possibly plugging in the cell 27 if the membrane swells from exposure to various liquids or is deformed by fluid flow.

EXAMPLE 1

The system shown in FIGS. 1 and 2 (including a 0.020 inch internal diameter and 0.025 inch external diameter tubular silicone rubber membrane 28 is used) is assembled and includes a Kratos Spectroflow 773 variable wavelength liquid chromatography detector 31 (set at 254 nanometers) and a Spectra Physics 4270 integrator-recorder 32. The receiving liquid 22 is water containing 75 percent, 50 percent, 35 percent or 20 percent acetonitrile by volume pumped at a flow rate of 200 microliters per minute. The sample loop 38 contains a fixed volume of 0.624 milliliter. The carrier liquid is deionized water pumped at a flow rate of 1.0 milliliter per minute.

Figure 3:
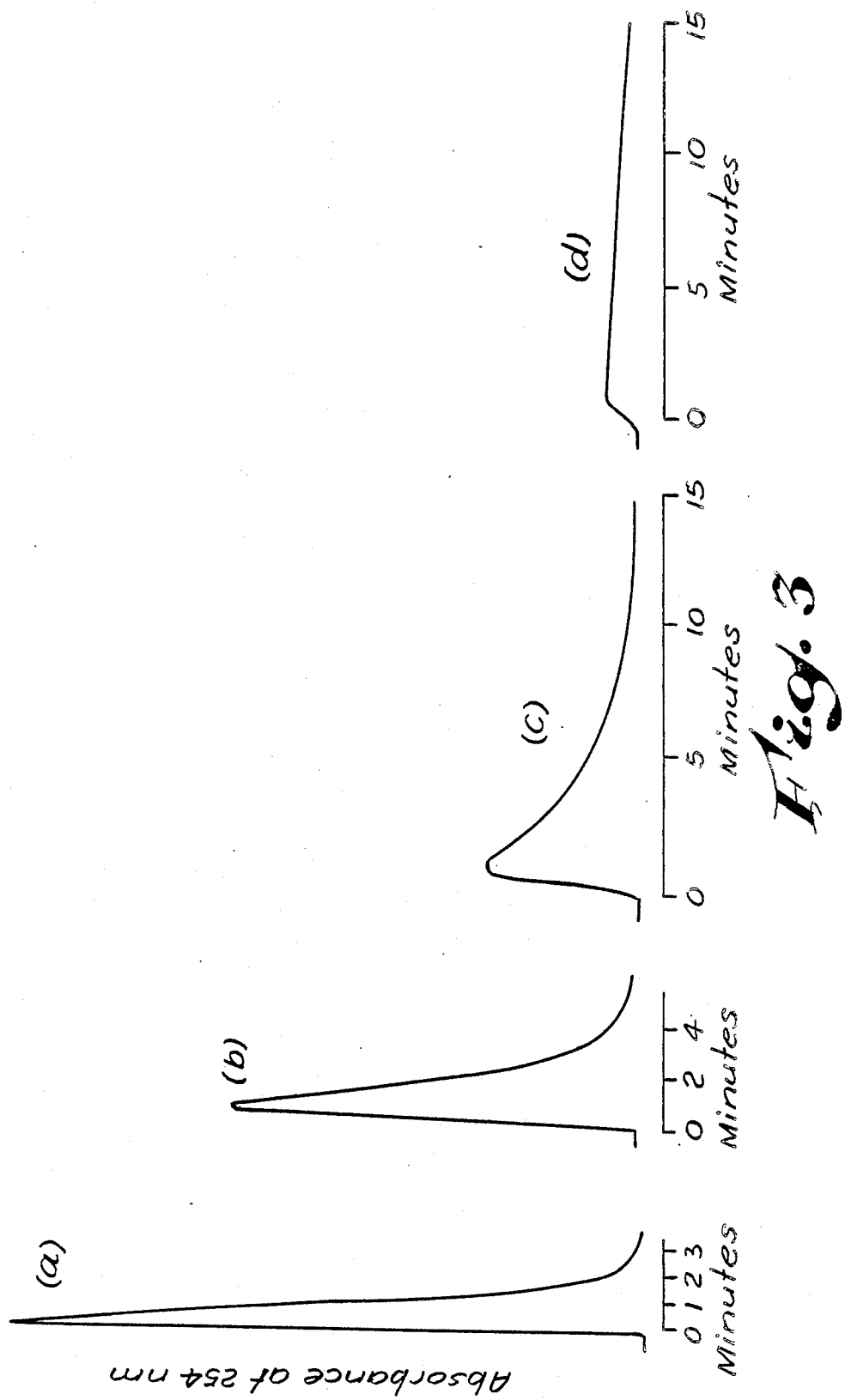
FIG. 3 (a)-(d) is a reproduction of the output of the integrator/recorder shown schematically in FIG. 1, when using the various receiving liquids as described in Example 1.

A sample containing 10 ppm (parts per million) of styrene monomer is flowed through line 41, while valve 20 is in the sample load position, thereby filling the sample loop 38. When valve 20 is switched to the inject position shown in FIG. 1, the sample is flowed by the carrier past and in contact with the membrane 28. The styrene monomer which permeates the membrane flows with the receiving liquid through the detector 31. The integrator/recorder 41 then traces the resulting dispersion of the concentration of styrene in the receiving liquid, i.e., styrene "peaks", as shown in FIG. 3 (a)-(d) when using an aqueous receiving liquid containing 75 percent acetonitrile (FIG. 3 (a)), 50 percent acetonitrile (FIG. 3 (b)), 35 percent acetonitrile (FIG. 3 (c)) or 20 percent acetonitrile (FIG. 3 (d)). Peaks obtained when using 75 percent or 50 percent acetonitrile are sharp and when triangulated, return to the baseline in less than 5 minutes. Peaks obtained when using 35 percent and 20 percent acetonitrile are much broader, less sensitive and when triangulated, return to the baseline in more than 5 minutes. The partition coefficient for FIG. 3 (a) is 1.1. The partition coefficient for FIG. 3 (b) is 3.2. The partition coefficient for FIG. 3 (c) is 13.7. The partition coefficient for FIG. 3 (d) is 65.

This example shows the critical nature of the partition coefficient of the receiving liquid in producing well defined, measurable flow injection peaks which rapidly return to baseline in the present method.

EXAMPLE 2

The same system as described in Example 1 is used, except the receiving liquid is deionized water containing 75 percent acetonitrile pumped at a flow rate of 0.20 milliliter per minute. The detector is set at 200 nm. The sample contains 10 ppm styrene monomer and 10 ppm 2,4-dichlorophenol and is adjusted to a pH of less than 5. The carrier liquid is deionized water adjusted to a pH of less than 5 and pumped at a flow rate of 1.0 milliliter per minute. Under these conditions both styrene monomer and 2,4-dichlorophenol permeate the membrane and cause a response peak at the detector when a 0.624 milliliter sample is injected into the carrier stream.

This example shows how to use the method of the present invention to determine the total of extractable neutral and acidic compounds in a mixture.

EXAMPLE 3

The same system as described in Example 2 is used except the detector is set to a wavelength of 254 nm and the sample and carrier liquid are adjusted to a pH of greater than 11. When 0.625 mL of a sample containing 10 ppm styrene monomer and 10 ppm 2,4-dichlorophenol is injected, a response peak from only the styrene monomer is observed because 2,4-dichlorophenol is not absorbed by the membrane under these conditions. In addition, the detector set at 254 nm is highly sensitive to styrene monomer and only slightly sensitive to 2,4-dichlorophenol.

This example shows how to use the present method to determine neutral compounds in the presence of acidic compounds.

EXAMPLE 4

The same system as described in Example 2 is used except the detector is set to a wavelength of 290 nm and the receiving liquid is water containing 0.01 N NaOH. The sample and the carrier liquid are adjusted to a pH of less than 5. When 0.625 mL of a sample containing 10 ppm styrene monomer and 10 ppm 2,4-dichlorophenol is injected, a response peak from only the 2,4-dichlorophenol is observed. Styrene monomer is not desorbed from the membrane under these conditions because of an unfavorable partition coefficient. The partition coefficient for 2,4-dichlorophenol is <0.1 and favorable. In addition, the detector set at 290 nm is highly sensitive to 2,4-dichlorophenol and only slightly sensitive to styrene monomer.

This example shows how to use the present invention to determine acidic compounds in the presence of neutral compounds.

EXAMPLE 5

The system of Example 1 is reproduced except that the membrane cell 27 is changed to include a silicone rubber membrane of 0.635 mm outside diameter, 0.305 mm inside diameter in its final and unstretched condition. Using a receiving liquid of 75 percent acetonitrile in water, a peak 36 mm tall is produced in less than 5 minutes.

Then the membrane is changed to include a silicone rubber membrane of 0.665 mm outside diameter, 0.350 mm inside diameter in a two-fold stretched condition. Using a receiving liquid of 75 percent acetonitrile in water, a peak 96 mm tall is produced at the same detector and recorder sensitivity as above. The peak is not only taller, its width is less, i.e., the peak returns to baseline faster.

This example shows the advantage of using a stretched membrane in the present invention.

What is claimed is:

1. A method for rapid and sensitive membrane assisted Flow Injection Analysis, comprising the steps of:
   (a) injecting a predetermined volume of a liquid sample into a flowing stream of liquid carrier to form a dispersion of the sample in the carrier, the sample containing a component of interest;
   (b) flowing the dispersion of the sample in the carrier into fleeting contact with one side of a two-sided membrane, the membrane absorbing at least a portion of the component of interest from the dispersion of the sample in the carrier to form a dispersion of the component of interest in the membrane;
   (c) contacting the other side of the membrane with a flowing stream of a receiving liquid, so that the dispersion of the component of interest in the membrane is essentially completely desorbed from the membrane in less than about 5 minutes and forming a dispersion of the component of interest in the receiving liquid, the partition coefficient of the component of interest between the membrane and the receiving liquid being less than about $1 \times 10^1$;
   (d) detecting the component of interest in the dispersion of the component of interest in the receiving liquid.

2. The method of claim 1 wherein the membrane used is a two-sided tubular membrane having an inside and an outside.

3. The method of claim 2 wherein the tubular membrane used is a silicone rubber tubular membrane.

4. The method of claim 3 wherein the tubular silicone rubber membrane used is a stretched silicone rubber tubular membrane.

5. The method of claim 1 wherein the membrane used is a two-sided planar silicone rubber membrane.

6. The method of claim 5 wherein the membrane used is a stretched planar silicone rubber membrane.

7. The method of claim 1 wherein the partition coefficient of the component of interest between the membrane and the receiving liquid is less than about 5.

8. The method of claim 1 wherein step (d) is accomplished using a flow-through photometric detector.

9. The method of claim 1 wherein in step (c) the component of interest is essentially completely desorbed from the membrane in less than about 2 minutes.

10. The method of claim 9 wherein the partition coefficient of the component of interest between the membrane and the receiving liquid is less than about 5.

* * * * *